United States Patent
Pav (10) Patent No.: US 8,292,809 B2
(45) Date of Patent: Oct. 23, 2012

(54) DETECTING CHEMICAL COMPONENTS FROM SPECTROSCOPIC OBSERVATIONS

(75) Inventor: Steven E Pav, San Francisco, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 871 days.

(21) Appl. No.: 12/412,956

(22) Filed: Mar. 27, 2009

(65) Prior Publication Data
US 2009/0247844 A1 Oct. 1, 2009

Related U.S. Application Data

(60) Provisional application No. 61/072,580, filed on Mar. 31, 2008.

(51) Int. Cl.
*A61B 5/1455* (2006.01)
(52) U.S. Cl. .................................. 600/309; 600/322
(58) Field of Classification Search .................. 600/309, 600/322, 323
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,773,422 A | 9/1988 | Isaacson et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,969,744 A | 11/1990 | Ordell |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |

(Continued)

FOREIGN PATENT DOCUMENTS

JP 3170866 7/1991

(Continued)

OTHER PUBLICATIONS

Wang, Lihong, et al.; "MCML—Monte Carlo Modeling of Light Transport in Multi-Layered Tissues," *Computer Methods and Programs in Biomedicine*, vol. 47, pp. 131-146 (1995).

(Continued)

*Primary Examiner* — Brian Szmal
*Assistant Examiner* — Michael C Stout (57) ABSTRACT

Embodiments disclosed herein may include methods and systems capable of estimating the underlying concentrations of chromophores in a sample. The photon scattering and absorption model may be based on Laplace and stable distributions, which may reveal that measurements in diffuse reflectance may follow a Beer-Lambert and Kohlrausch-Williams-Watts (KWW) product. This Beer-Lambert portion of the product may dominate in high absorption sample areas, while the KWW portion of the product may dominate in low absorption sample areas.

17 Claims, 3 Drawing Sheets

U.S. PATENT DOCUMENTS

| | | |
|---|---|---|
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Kuenstner |
| 5,694,931 A | 12/1997 | Tsuchiya |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,853,364 A | 12/1998 | Baker, Jr. et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,075,610 A | 6/2000 | Ueda et al. |
| 6,081,742 A | 6/2000 | Amano et al. |
| 6,083,172 A | 7/2000 | Baker, Jr. et al. |
| 6,088,607 A | 7/2000 | Diab et al. |
| 6,120,460 A | 9/2000 | Abreu |
| 6,134,460 A | 10/2000 | Chance |
| 6,135,952 A | 10/2000 | Coetzee |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,335,792 B1 | 1/2002 | Tsuchiya |
| 6,353,750 B1 | 3/2002 | Kimura et al. |
| 6,397,091 B2 | 5/2002 | Diab et al. |
| 6,402,986 B1 | 6/2002 | Jones, II et al. |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,567,165 B1 | 5/2003 | Tsuchiya et al. |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,721,584 B2 | 4/2004 | Baker, Jr. et al. |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,836,679 B2 | 12/2004 | Baker, Jr. et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,987,994 B1 | 1/2006 | Mortz |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,127,278 B2 | 10/2006 | Melker et al. |
| 7,162,306 B2 | 1/2007 | Caby et al. |
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |

| | | |
|---|---|---|
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0025931 A1 | 2/2006 | Rosen et al. |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2008/0081974 A1 | 4/2008 | Pav |

FOREIGN PATENT DOCUMENTS

| | | |
|---|---|---|
| JP | 3238813 | 10/1991 |
| JP | 4332536 | 11/1992 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| WO | WO9309711 | 5/1993 |
| WO | WO9843071 | 10/1998 |
| WO | WO9932030 | 7/1999 |
| WO | WO0021438 | 4/2000 |

OTHER PUBLICATIONS

Barreto, Armando B., et al.; "Adaptive LMS Delay Measurement in dual Blood Volume Pulse Signals for Non-Invasive Monitoring," *IEEE*, pp. 117-120 (1997).

Leahy, Martin J., et al.; "Sensor Validation in Biomedical Applications," *IFAC Modeling and Control in Biomedical Systems*, Warwick, UK; pp. 221-226 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

Wang, Lihong, et al.; "CONV-Convolution for Responses to a Finite Diameter Photon Beam Incident on Multi-Layered Tissues," *Computer Methods and Programs in Biomedicine* 54, pp. 141-150 (1997).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Lutter, N., et al.; "Comparison of Different Evaluation Methods for a Multi-Wavelength Pulse Oximeter," *Biomedizinische Technik*, vol. 43, (1998).

Todd, Bryan, et al.; "The Identification of Peaks in Physiological Signals," *Computers and Biomedical Research*, vol. 32, pp. 322-335 (1999).

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Berberan-Santos, Mario N.; "Analytical Inversion of the Laplace Transform Without Contour Integration: Application to Luminescence Decay Laws and Other Relaxation Functions," *Centro de Quimica-Fisica Molecular, Instituto Superior Técnico*, 1049-001 Lisboa, Portugal; Journal of Mathematical Chemistry, vol. 38, No. 2, (Aug. 2005).

Berberan-Santos, Mario N., "Relation Between the Inverse Laplace Transforms of $I(t^B)$ and $I(t)$: Application to the Mittag-Leffler and Asymptotic Inverse Power Law Relaxation Functions," *Centro de Quimica-Fisica Molecular, Instituto Superior Técnico*, 1049-001 Lisboa, Portugal (Aug. 2005).

Kim, J.M., et al.; "Signal Processing Using Fourier & Wavelet Transform," pp. II-310-II-311 (undated).

DETECTING CHEMICAL COMPONENTS FROM SPECTROSCOPIC OBSERVATIONS

RELATED APPLICATIONS

This application claims priority to U.S. Provisional Application No. 61/072,580, filed Mar. 31, 2008, and is incorporated herein by reference in its entirety.

BACKGROUND

The present disclosure relates generally to the field of spectroscopy and, more particularly, to a system and method of optimizing the processing spectroscopic data.

This section is intended to introduce the reader to various aspects of art that may be related to various aspects that are described and/or claimed below. This discussion is believed to be helpful in providing the reader with background information to facilitate a better understanding of these various aspects. Accordingly, it should be understood that these statements are to be read in this light, and not as admissions of prior art.

Spectroscopy may be employed to ascertain the existence and/or concentration of component chemicals in a sample. To perform a spectroscopic analysis on a sample, a source may first send electromagnetic radiation through the sample. The spectrum of electromagnetic radiation which passes through the sample may indicate the absorbance of the sample. Based on the amount and spectrum of the sample absorbance, the presence and/or concentration of distinct chemicals may be detected by employing methods of spectrographic data processing.

Typically, the analysis includes modeling the underlying concentrations of chromophores in a sample from spectroscopic observations. The most common method for estimating these chromophores concentrations includes applying a photon scattering and absorption model based solely on the Beer-Lambert Law and utilizing multiple linear regression techniques to approximate the chromophores concentrations. However, the current methods may result in errors on the order of several percent. As such, a method and system for closer approximation of underlying concentrations of chromophores in a sample from spectroscopic observations is needed.

SUMMARY

Certain aspects commensurate in scope with the originally claimed subject matter are set forth below. It should be understood that these aspects are presented merely to provide the reader with a brief summary of certain embodiments and that these aspects are not intended to limit the scope of the claims. Indeed, the claims may encompass a variety of aspects that may not be set forth below.

In accordance with an embodiment, a method of processing spectrographic data may include transmitting an optical signal from an emitter to a sample, receiving the optical signal having passed through the sample at a detector, and analyzing the data associated with the received sample by numerically calculating an approximation of underlying concentrations of chromophores by applying a photon scattering and absorption model based on a mixed Beer-Lambert/Kohlrausch-Williams-Watts Model (KWW) for photon diffusion. In a another embodiment, a method for using Kernel Partial Least Squares (KPLS) Regression to formulate a model to be used in conjunction with analyzing spectrographic data includes collecting a number of data samples of optical signals passed through a sample from an emitter to a detector, measuring an affine function of the concentrations of the components for each given sample, and performing a KPLS regression to find a model for estimating future spectroscopic data.

BRIEF DESCRIPTION OF THE DRAWINGS

Certain embodiments may be understood upon reading the following detailed description and upon reference to the drawings in which.

DETAILED DESCRIPTION

Various embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is related to a photon scattering and absorption model which may be applied as an alternative to a strict application of the Beer-Lambert Law for estimation of the underlying concentrations of chromophores in a sample. The photon scattering and absorption model may be based on Laplace and stable distributions which reveal that measurements in diffuse reflectance may follow a Beer-Lambert and Kohlrausch-Williams-Watts (KWW) product. This Beer-Lambert portion of the product may dominate in high absorption sample areas, while the KWW portion of the product may dominate in low absorption sample areas.

Figures 1, 1A:
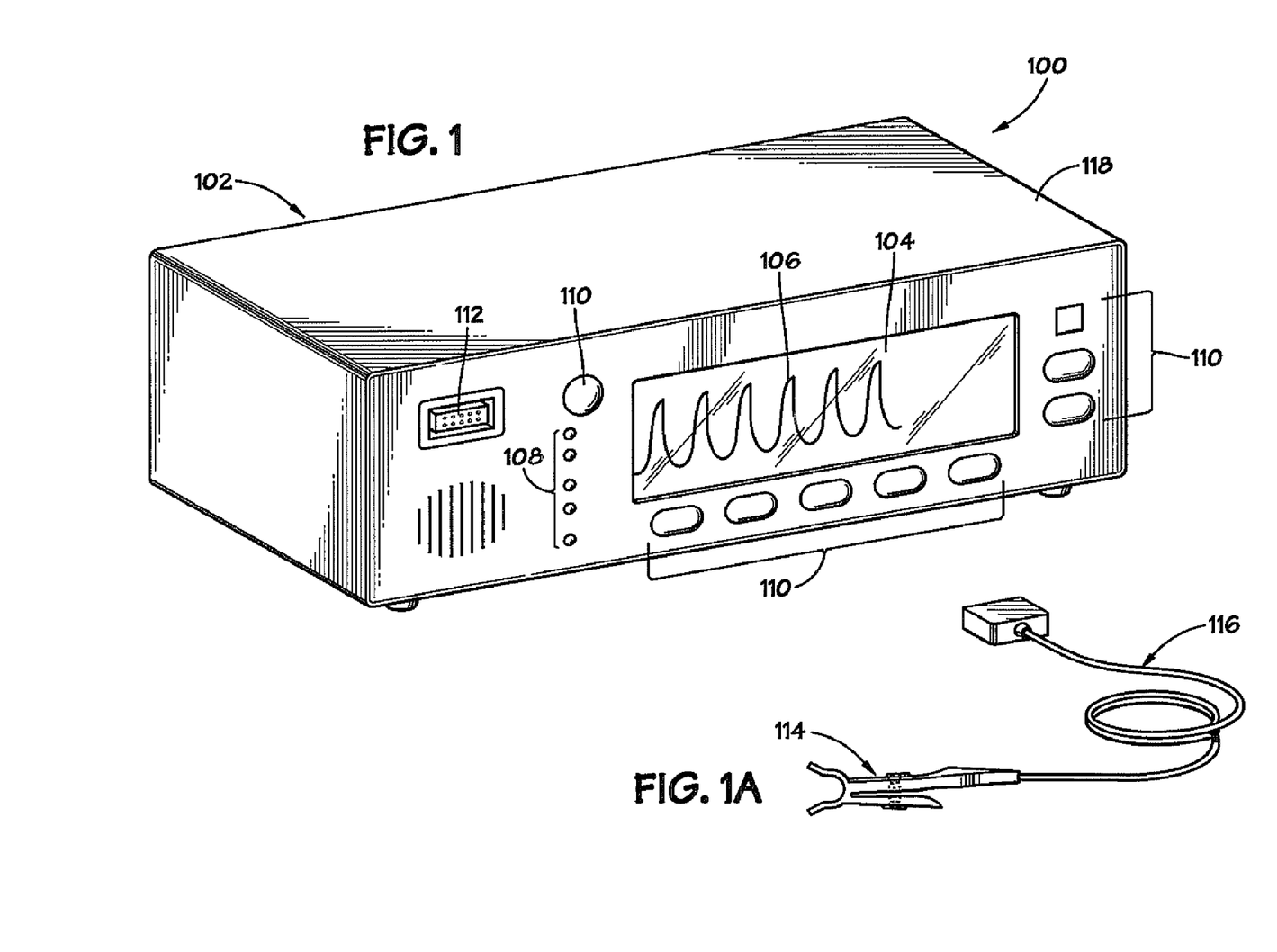
FIG. 1 illustrates a perspective view of a pulse oximeter in accordance with an embodiment.
FIG. 1A illustrates a perspective view of a sensor in accordance with the pulse oximeter illustrated in FIG. 1.

Turning to FIG. 1, a perspective view of a medical device is illustrated in accordance with an embodiment. The medical device may be a pulse oximeter 100. The pulse oximeter 100 may include a monitor 102. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 118. The casing 118 may aid in the protection of the internal elements of the monitor 102 from damage.

The monitor 102 may further include a sensor port 112. The sensor port 112 may allow for connection to an external sensor. FIG. 1A illustrates a sensor 114 that may be used with the monitor 102. The sensor 114 may be communicatively coupled to the monitor 102 via a cable 116 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient. The sensor 114 and the monitor 102 may combine to form the pulse oximeter 100.

Figure 2:
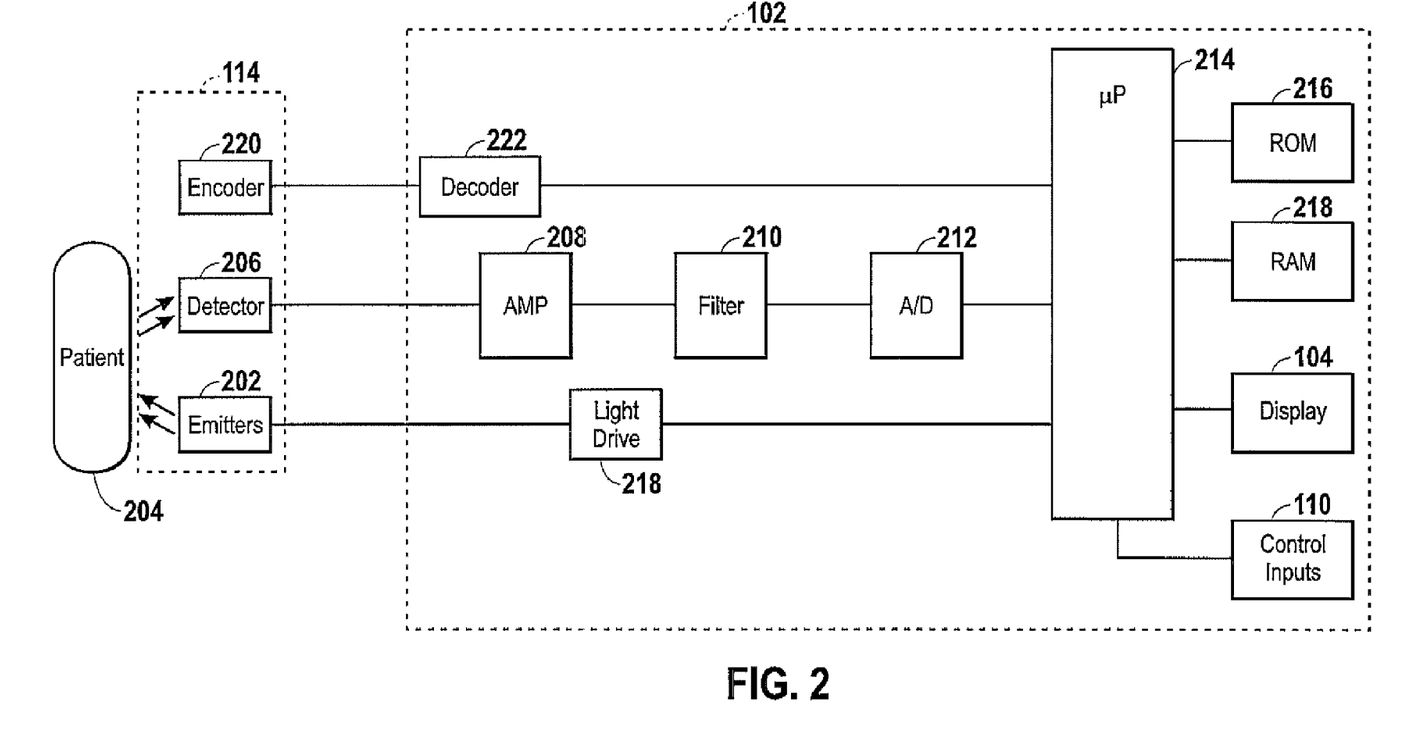
FIG. 2 illustrates a simplified block diagram of a pulse oximeter in FIG. 1, according to an embodiment.

Turning to FIG. 2, a simplified block diagram of a medical device is illustrated in accordance with an embodiment. The medical device may be the pulse oximeter 100. The pulse oximeter 100 may include a sensor 114 having one or more emitters 202 configured to transmit electromagnetic radiation, i.e., light, into the tissue of a patient 204. For example, the emitter 202 may include a plurality of LEDs operating at discrete wavelengths, such as in the red and infrared portions of the electromagnetic radiation spectrum. Alternatively, the emitter 202 may be a broad spectrum emitter, or it may include wavelengths for measuring water fractions.

The sensor 114 may also include one or more detectors 206. The detector 206 may be a photoelectric detector which may detect the scattered and/or reflected light from the patient 204. Based on the detected light, the detector 206 may generate an electrical signal, e.g., current, at a level corresponding to the detected light. The sensor 114 may direct the electrical signal to the monitor 102 for processing and calculation of physiological parameters.

In this embodiment, the monitor 102 may be a pulse oximeter, such as those available from Nellcor Puritan Bennett L.L.C. The monitor 102 may include a light drive unit 218. Light drive unit 218 may be used to control timing of the emitter 202. An encoder 220 and decoder 222 may be used to calibrate the monitor 102 to the actual wavelengths being used by the emitter 202. The encoder 220 may be a resistor, for example, whose value corresponds to the actual wavelengths and to coefficients used in algorithms for computing the physiological parameters. Alternatively, the encoder 220 may be a memory device, such as an EPROM, that stores wavelength information and/or the corresponding coefficients. For example, the encoder 220 may be a memory device such as those found in OxiMax® sensors available from Nellcor Puritan Bennett L.L.C. The encoder 220 may be communicatively coupled to the monitor 102 in order to communicate wavelength information to the decoder 222. The decoder 222 may receive and decode the wavelength information from the encoder 220. Once decoded, the information may be transmitted to the processor 214 for utilization in calculation of the physiological parameters of the patient 108.

Further, the monitor 102 may include an amplifier 208 and a filter 124 for amplifying and filtering the electrical signals from the sensor 114 before digitizing the electrical signals in the analog-to-digital converter 212. Once digitized, the signals may be used to calculate the physiological parameters of the patient 204. The monitor 102 may also include one or more processors 214 configured to calculate physiological parameters based on the digitized signals from the analog-to-digital converter 212 and further using algorithms programmed into the monitor 102. The processor 214 may be connected to other component parts of the monitor 102, such as one or more read only memories (OM) 216, one or more random access memories (RAM) 218, the display 104, and the control inputs 110. The ROM 216 and the RAM 218 may be used in conjunction, or independently, to store the algorithms used by the processors in computing physiological parameters. The ROM 216 and the RAM 218 may also be used in conjunction, or independently, to store the values detected by the detector 206 for use in the calculation of the aforementioned algorithms.

In an embodiment, the algorithm stored in the ROM 216 for use by the processor 214 to compute physiological parameters may be a Beer-Lambert and Kohlrausch-Williams-Watts (KWW) product for measuring characteristics of a sample, such as chromophore concentrations in a patient 204. The probability that an emitted photon passes through a sample and arrives at a detector 206 is $$I(\mu_a, \mu_s, g) = \int_0^\infty e^{-x\mu_a} f(x) dx.$$

In this expression, $\mu_s$ may represent the scattering coefficient of the medium and g may represent the anisotropy coefficient of the medium. Furthermore, $\mu_a$ may be the absorption coefficient. This expression may be derived by assuming that f is the density function for photon path lengths for a fixed configuration of an emitter 202, a detector 206, and a sample site, for example, on a patient 204. Assuming that the medium is non-absorbing at the given wavelength supplied by the emitter 202, i.e $\mu_a=0$, then the function for determining the probability of a photon passing through a the zero absorption sample across a distance 1, where l is a distance between a to b, (where a to b may be the maximum distance through the medium between the emitter 202 and the detector 206), may be found by $$\int_a^b f(x) dx.$$

Therefore, in the absence of absorption, $$I(0, \mu_s, g) = \int_0^\infty f(x) dx,$$

where $I(\mu_a, \mu_s, g)$ represents the detected intensity at the detector 206 for the given absorption, scattering, and anisotrophy coefficients $\mu_a$, $\mu_s$, and g. However, real world situations may occur where the absorption coefficient does not equal zero.

In the case where absorption does not equal zero, according to the Beer-Lambert Law, the probability that a single photon traveling a distance l through a medium with an absorption coefficient of $\mu_a$ will be absorbed is equal to $e^{-l\mu_a}$, which follows from the memoryless property and definition of $\mu_a$. Combined, this yields $$I(\mu_a, \mu_s, g) = \int_0^\infty e^{-x\mu_a} f(x) dx.$$

Moreover, $I(\mu_a, \mu_s, g)$, may then be the Laplace transform of $f$, i.e. $I(\mu_a, \mu_s, g) = L\{f\}(\mu_a)$. Thus, the probability that an emitted photon passes through the sample of, for example, a patient 204 is $$\int_0^\infty e^{-x\mu_a} f(x) dx = \mathcal{L}\{f\}(\mu_a).$$

Moreover, the path length distribution function, $f(x)$, may be shown to follow a sum-stable distribution. The Laplace transform of a stable distribution with a parameter a is $e^{-s^\alpha}$. Therefore, since $f(x)$ follows a stable distribution, then $I(\mu_a, \mu_s, g)$ should contain a factor of the form $e^{-\mu_a^\beta}$. Modeling $f(x)$ for the KWW distribution results in $$I(\mu_s,\mu_s,g)=C_1(\mu_s,g)e^{-C2(\mu_s,g)\mu_a^\beta}.$$

In this equation, $C_1(\mu_s, g)$ may be strictly due to scattering and the geometry of the emitter 202, the detector 206, and a sample site, for example, on a patient 204. However, since $f(x)=0$ for all x smaller than the Euclidian distance from the source to the detector, $f(x)$ should be a shift of a stable distribution. Addition of an extra factor of $e^{-C_3\mu_\alpha}$ to the Laplace transform compensates for the shift, where $C_3$ may represent the offset distance. The offset distance may be equal to the Euclidean distance between the emitter 202 and the detector 206. Inclusion of the shift factor results in $$I(\mu_a,\mu_s,g)=C_1(\mu_s,g)e^{-(C2(\mu_s,g)\mu_a^\beta+C_3\mu_a)}.$$

In this embodiment, the model can be extended to include the case of collimated, i.e. non-diffused, light where some of the light detected has not been scattered, while other portions of the light has been scattered. For this embodiment, the path length distribution function, $f(x)$, can be described as $$f(x)=g(x)+C_4 e^{-C_3\mu_s\delta}(x-C_3).$$

Here, $g(x)$ may be a stable distribution, $C_4$ may represent a coefficient inclusive of the intensity of the emitter 202 and the coupling efficiency of the test geometry, and $\delta(x)$ may be the Dirac delta. The coupling efficiency of the test geometry may take include such factors as the aperature size of the detector 206 as well as the beam diameter. By the linearity of the Laplace transform, this yields $$I(\mu_a,g)=C_1(\mu_s,g)e^{-(C_2(\mu_s,g)\mu_a^\beta+C_3\mu_a)}+C_4 e^{-C_3(\mu_s+\mu_a)}.$$

This equation represents the general attenuated KWW model for the detected intensity at the detector 206 for the given absorption, scattering, and anisotrophy coefficients $\mu_a$, $\mu_s$, and g. This general attenuated KWW model may be stored in the ROM 216 for use by the processor 214 in calculating physiological parameters based on the digitized signals from the analog-to-digital converter 212.

In an embodiment (in the case of diffuse reflectance), the second summand equals zero, for the case when the detector 206 may not be located in the beam path of the emitter 202. The log of the general attenuated KWW model may be taken, resulting in $$-\log I(\mu_a,\mu_s,g)=-\log C_1(\mu_s,g)+C_2(\mu_s,g)\mu_a^\beta+C_3\mu_a.$$

Figure 3:
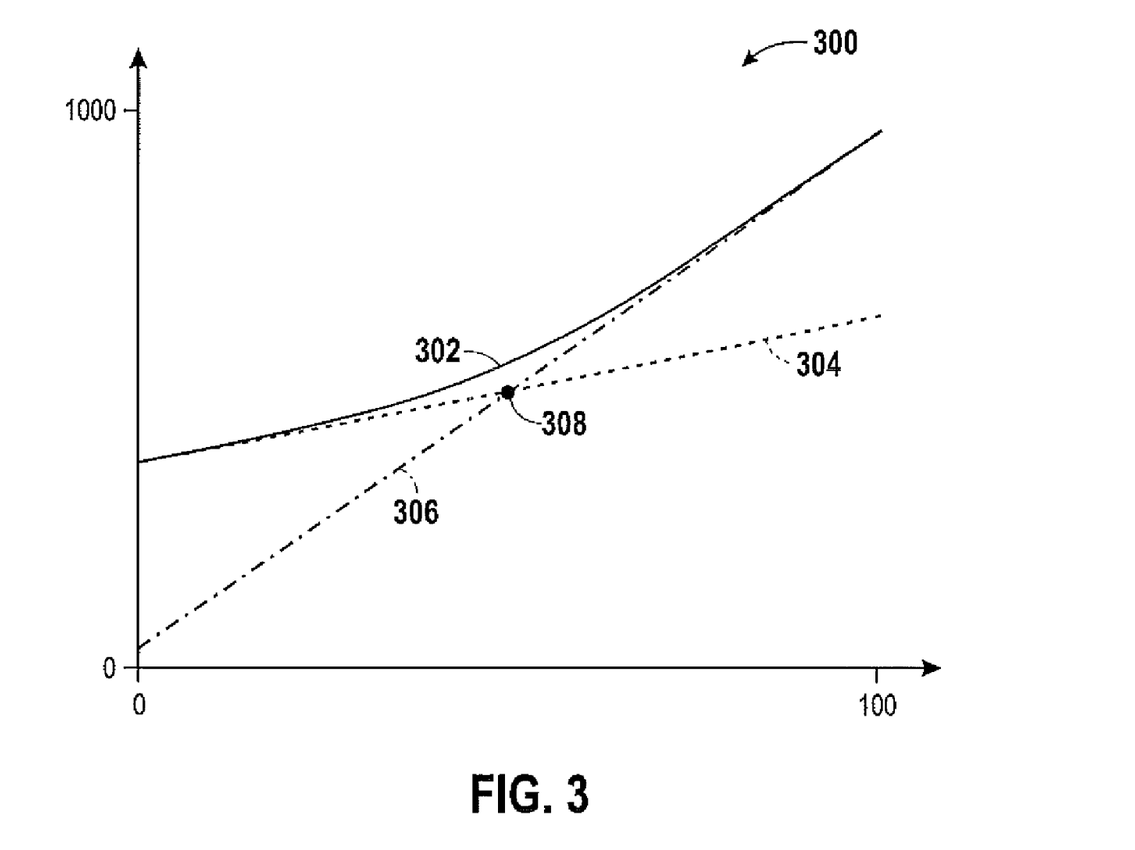
FIG. 3 illustrates a graph of diffuse reflectance of a sample area measured by the pulse oximeter in FIG. 1, according to an embodiment.

As $\log C_1(\mu_s, g)$ can be estimated, then $\log C_1(\mu_s, g) - \log I(\mu_a, \mu_s, g)$ versus $\mu_a$ may be plotted graphically. FIG. 3 illustrates a graph 300 of $\log C_1(\mu_s, g) - \log I(\mu_a, \mu_s, g)$ versus $\mu_a$. As seen from the graph 300, diffuse reflectance 302 may closely follow the predicted KWW model 304 of diffuse reflectance in sample areas with low absorption rates. Conversely, diffuse reflectance 302 may closely follow the predicted Beer-Lambert model 306 of diffuse reflectance in sample areas with high absorption rates. The crossover point 308 where the two terms trade dominance occurs at $$\mu_a = (C_2(\mu_s, g)/C_3)^{\frac{1}{1-\beta}},$$

while far from the crossover point on each end of the diffuse reflectance 302 may be well approximated by the summands $C_2(\mu_s, g)\mu_a^\beta$ for the predicted KWW model 304, and $C_3\mu_a$ for the Beer-Lambert model 306.

The tendencies of the KWW model 304 and the Beer-Lambert model 306 may be used in the estimation of the concentrations of chemical components of known absorptions. Thus, when a sample consists of l chemical components of varying concentrations c may be subject to light of different wavelengths, and the intensity at the detector 206 has been recorded, then the bulk absorption coefficient may be proportional to $U_a c$, where $U_a$ represents the matrix of absorption coefficients of the different components l. If $\mu_s$ is taken to vary slowly with respect to the wavelength, then the offset and scaling factors will vary slowly with respect to the wavelength, and may be approximated with, for example, B-splines or quadratic polynomials. Thus, the general attenuated KWW model becomes $$m=F_1 c_1+(F_2 c_2)\odot(U_a c)^\beta+C_3(U_a c),$$

where m represents the vector of the negative log intensity values, $F_1$ and $F_2$ may represent matrices whose columns span the spaces containing the approximations of offset and scaling values, and "$\odot$" represents the Hadamard, i.e. element by element, product. Furthermore, $(U_a c)^\beta$ may be a Hadamard exponential.

For given estimates of c and $\beta$, the optimal values for $c_1$ and $c_2$ may be easily computed. Thus, determining the values used as estimations for c and $\beta$ remains. Let $\hat{c}, \hat{\beta}, \hat{c}_1, \hat{c}_2, \hat{C}_3$ represent estimates of the unknown quantities. The residual may then be defined as $$\epsilon=m-F_1\hat{c}_1-(F_2\hat{c}_2)\odot(U_a\hat{c})-\hat{C}_3(U_a\hat{c}),$$

while the square error of the approximation may be $$\phi(\hat{c}_1,\hat{c}_2,\hat{C}_3,\hat{c},\hat{\beta})=\epsilon^T\epsilon$$

Therefore, to find the $\hat{c}_1 \hat{c}_2$ and $\hat{C}_3$, which minimize $\odot$ for fixed $\hat{c}, \hat{\beta}$, we may estimate the vector of the negative log intensity values as $$m \approx F_1\hat{c}_1 + \text{diag}((U_a\hat{c})^{\hat{\beta}})F_2\hat{c}_2 + \hat{C}_3 U_a\hat{c} =$$

$$\left[F_1 \text{diag}((U_a\hat{c})^{\hat{\beta}})F_2 U_a\hat{c}\right]\begin{bmatrix}\hat{c}_1\\\hat{c}_2\\\hat{C}_3\end{bmatrix} = A\begin{bmatrix}\hat{c}_1\\\hat{c}_2\\\hat{C}_3\end{bmatrix},$$

where diag (v) represents the square diagonal matrix with diagonal v and $A=(\hat{c},\hat{\beta})=$ $$A=(\hat{c},\hat{\beta})=[F_1 \text{diag}((U_a\hat{c}))F_2 U_a\hat{c}].$$

The least squares optimal $\hat{c}_1\hat{c}_2$ and $\hat{C}_3$ can then be described by the normal equation form $$\begin{bmatrix} \hat{c}_1 \\ \hat{c}_2 \\ \hat{C}_3 \end{bmatrix} = (A^T A)^{-1} A^T m.$$

In an embodiment, the least squares solution may be calculated by the processor 214 using a software program which may be stored on ROM 216.

φ may be considered a function of ĉ and $\hat{\beta}$. Optimization of φ may be accomplished by an iterative numerical scheme used to compute the gradient of the objective with respect to the vector of free variables. In an embodiment, the iterative numerical scheme used may be the Broyden-Fletcher-Goldfarb-Shanno (BFGS) method. In another embodiment, the iterative numerical scheme used may be the conjugate gradient method. The gradient will depend on $\hat{c}_1$, $\hat{c}_2$, and $\hat{C}_3$, and in an embodiment, the partial derivatives of $\hat{c}_1$, $\hat{c}_2$, and $\hat{C}_3$ may be incorporated into the computation. In another embodiment, computational time may be reduced by approximating the gradient by assuming fixed values for $\hat{c}_1$, $\hat{c}_2$, and $\hat{C}_3$. Under this assumption, the gradients of φ, which can be used to minimize φ with respect to ĉ and $\hat{\beta}$, can be found from $$\frac{\partial \phi(\hat{c}_1, \hat{c}_2, \hat{C}_3, \hat{c}, \hat{\beta})}{\partial \hat{\beta}} = -2\left(\epsilon \odot F_2 \hat{c}_2 \odot (U_a \hat{c})^{\hat{\beta}}\right)^T \log(U_a \hat{c})$$

and $$\nabla_{\hat{c}} \phi(\hat{c}_1, \hat{c}_2, \hat{C}_3, \hat{c}, \hat{\beta}) = -2 U_a^T (\hat{\beta} \epsilon \odot F_2 \hat{c}_2 \odot (U_a \hat{c})^{\hat{\beta}-1} + \hat{C}_3 \epsilon).$$

When the processor 214 determines that the $\mu_a$ values fall into the dominant region of either the predicted KWW model 304 or the predicted Beer-Lambert model 306, the final summand of $$m = F_1 C_1 + (F_2 C_2) \odot (U_a c)^{\beta} + C_3 (U_a c)$$

may be eliminated. For example, when the Beer-Lambert model 306 dominates, then $\hat{\beta}$ may tend towards "1". Assuming that the space spanned by the columns of $F_2$ represent a constant, which occurs if $F_2$ spans a B-spline or a polynomial space (in $\mu_a$). In this form, $\hat{c}_1$ and $\hat{c}_2$ may be found by $$\begin{bmatrix} \hat{c}_1 \\ \hat{c}_2 \end{bmatrix} = (B^T B)^{-1} B^T m,$$

where $$B = B(\hat{c}, \hat{\beta}) = \left[ F_1 \text{diag}\left((U_a \hat{c})^{\hat{\beta}}\right) F_2 \right].$$

This results in the gradients of φ being solved by $$\frac{\partial \varnothing(\hat{c}_1, \hat{c}_2, \hat{c}, \hat{\beta})}{\partial \hat{\beta}} = -2\left(\epsilon \odot F_2 \hat{c}_2 \odot (U_a \hat{c})^{\hat{\beta}}\right)^T \log(U_a \hat{c})$$

and $$\nabla_{\hat{c}} \phi(\hat{c}_1, \hat{c}_2, \hat{c}, \hat{\beta}) = 2 \hat{\beta} U_a^T (\epsilon \odot F_2 \hat{c}_2 \odot (U_a \hat{c})^{\hat{\beta}-1}).$$

In another embodiment, a method for using KPLS Regression to formulate a model to be used in conjunction with analyzing spectrographic data may be employed. This method may include the preprocessing of the data with a nonlinear transform to a given space before performing the linear regression into that same space. This may be achieved by use of a kernel function, κ, which may be used to compute the dot product in the given space of two vectors in the data space, without having to perform a transform on that space. This may be accomplished by building a nonlinear model, which may begin with y, some affine function of the concentrations of the components of a given sample. The KPLS may proceed by collecting a number of data samples of optical signals passed through a sample from an emitter 202 to a detector 206 and measured, for example, spectrographically. The processor 214 may then measure an affine function y of the concentrations of the components for each given sample and store it in a vector y. The processor 214 may performing a KPLS regression to find a model of the form $$y_i \approx y_0 + \sum_j \alpha_j k(X_{j,:} X_{i,:})$$

This model may then be used to estimate y.

To determine κ, we can set a value for β, or we may determine it from the procedure described above. In either case, an x measurement should take the form of $$x = h + m(\mu_a^T c)^{\beta}.$$

Since a lower bound on h can be determined for a given sensor 114, its value may be set as small relative to the second summand. From $$\mu_a^T c = [(x-h)/m]^{1/\beta},$$

using a Taylor expansion, we may determine $$\mu_a^T c \approx \frac{1}{m} \frac{1}{x^{\frac{1}{\beta}}} \left[ x^{\frac{1}{\beta}} - \frac{1}{\beta} x^{\frac{1}{\beta}-1} h \right].$$

This suggests the use of $$\kappa(x, y) = (x^T y)^{\frac{1}{\beta}} \text{ or } \kappa(x, y) = (x^T y)^{\frac{1}{\beta}} + (x^T y)^{\frac{1}{\beta}-1}$$

as kernels.

A specific embodiment may include β=½, where $\mu_s$, and g are fixed. In this case, the function $$(C_2(\mu_s, g)\mu_a^{\beta} + C_3 \mu_a)$$

may be an injunctive function, i.e. one-to-one, with respect to $\mu_a$. Thus, the function has an inverse. As such, an optical observation may be transformed to a quantity proportional to $\mu_a$, thus linearizing the signal. Therefore, once $C_1(\mu_s, g)$ is estimated, the quantity $$M(\mu_a; \mu_s, g) =_{df} \log C_1(\mu_s, g) - \log I(\mu_a, \mu_s, g) = C_2(\mu_s, g)\mu_a^{\beta} + C_3 \mu_a$$

may be computed from the optical observations of $I(\mu_a, \mu_s, g)$. Moreover, since β=½, the observations are explicitly invertible to $$M(\mu_a; \mu_s, g) = C_2(\mu_s, g)\mu_a^{\frac{1}{2}} + C_3 \mu_a$$

-continued
$$0 = C_3(\sqrt{\mu_a})^2 + C_2(\mu_s, g)\sqrt{\mu_a} - M(\mu_a; \mu_s, g)$$

The quadratic equation may be used to yield:

$$\sqrt{\mu_a} = \frac{-C_2(\mu_s, g) \pm \sqrt{C_2(\mu_s, g)^2 + 4C_3 M(\mu_a; \mu_s, g)}}{2C_3},$$

the negative root of which may be ignored to generate $$\sqrt{\mu_a} = -\frac{C_2(\mu_s, g)}{2C_3} + \sqrt{\left(\frac{C_2(\mu_s, g)}{2C_3}\right)^2 + \frac{M(\mu_a; \mu_s, g)}{C_3}}.$$

Furthermore, by letting $\kappa = C_2(\mu_s, g)/2C_3$, the equation becomes:

$$\mu_a = \left(-\kappa + \sqrt{\kappa^2 + \frac{M(\mu_a; \mu_s, g)}{C_3}}\right)^2 =$$

$$2\kappa^2 + \frac{M(\mu_a; \mu_s, g)}{C_3} - 2\kappa\sqrt{\kappa^2 + \frac{M(\mu_a; \mu_s, g)}{C_3}}.$$

Accordingly, because $C_1(\mu_s, g)$ and $C_2(\mu_s, g)$ may depend on geometry and scattering, while $C_3$ may depend on the test geometry, only the estimation of $\mu_s$, and g is required to be made by the pulse oximeter 100. This may be accomplished through assumptions as to the tissue sample of the patient 204 which may be stored in the ROM 216 and/or the RAM 218 for use in the calculation of $\mu_a$.

Another embodiment may be applied when observations are made over time with changes in the absorption of the medium and negligible changes in the scattering properties of the medium. For $$-\frac{\partial \log J(\mu_a, \mu_s, g, t)}{\partial t} = C_2(\mu_s, g)\beta \mu_a^{\beta-1}\frac{\partial \mu_a}{\partial t} + C_3\frac{\partial \mu_a}{\partial t},$$

it may be shown that $$-\frac{\partial \log J(\mu_a, \mu_s, g, t)}{\partial t}$$

may be large when $\mu_a$ is small, which contrasts with the expected values from the Beer-Lambert Law that $$-\frac{\partial \log J(\mu_a, \mu_s, g, t)}{\partial t} = C_3\frac{\partial \mu_a}{\partial t}.$$

holds steady for all values of $\mu_a$. When observations are made at n wavelengths over a sample containing/chemical components of varying concentrations c(t), with $U_a$ as the (n×l) matrix of absorption coefficients of the different components at the different wavelengths, then the vector of $\mu_a$ at the n wavelengths is $U_a c(t)$. If m is the n-vector of observed $$-\frac{\partial \log J(\mu_a, \mu_s, g, t)}{\partial t}$$

values at a fixed time at the given wavelength, then $$m = [C_2(\mu_s, g)\beta(U_a c(t))^{\beta-1} + C_3\vec{I}] \odot U_a \frac{\partial c(t)}{\partial t}.$$

As such, when $U_a c(t)$ is estimated, then the left Hadamard multiplicand may be estimated, resulting in $$g \approx C_2(\mu_s, g)\beta(U_a c(t))^{\beta-1} + C_3\vec{I} \text{ and } m \approx (\text{diag}(g)U_a)\frac{\partial c(t)}{\partial t}$$

for which $$\frac{\partial c(t)}{\partial t}$$

be estimated, for example, using the least squares method.

Specific embodiments have been shown by way of example in the drawings and have been described in detail herein. However, it should be understood that the claims are not intended to be limited to the particular forms disclosed. Rather the claims are to cover all modifications, equivalents, and alternatives falling within their spirit and scope.

What is claimed is:

1. A medical device, comprising:
   a monitor adapted to receive a physiologic signal from a patient; and
   a processor capable of determining physiological characteristics of the patient based at least in part on the physiologic signal by applying a mixed Beer-Lambert/Kohlrausch-Williams-Watts Model (KWW) algorithm for photon diffusion to the physiologic signal.

2. The medical device of claim 1, wherein the processor is capable of determining an absorption rate of a sample area of the patient from the physiologic signal.

3. The medical device of claim 2, wherein the processor is capable of applying a predicted KWW model of diffuse reflectance when the absorption rate is determined to fall below a threshold value.

4. The medical device of claim 1, comprising a memory device capable of storing the threshold value as a value determined by the processor based at least in part upon the physiologic signal.

5. The medical device of claim 2, wherein the processor is capable of storing a predicted Beer-Lambert model of diffuse reflectance when the absorption rate is
determined to be above a threshold value.

6. The medical device of claim 5, comprising a memory device capable of storing the threshold value as a preprogrammed value.

7. The medical device of claim 1, wherein the processor is capable of determining concentrations of chromophores in a sample area of the patient based at least in part upon the mixed Beer-Lambert/KWW algorithm.

8. The medical device of claim 1, comprising a sensor capable of emitting electromagnetic radiation into a tissue sample of the patient, and detecting the scattered and/or reflected light from the tissue sample.

9. The medical device of claim 8, wherein the sensor is capable of generating the physiologic signal corresponding to the scattered and/or reflected light detected, and directing the physiologic signal to the monitor.

10. A method of calculating physiological characteristics of a patient, comprising:
   obtaining a physiologic signal from a patient;
   calculating physiological characteristics of the patient based at least in part on the physiologic signal by applying a mixed Beer-Lambert/Kohlrausch-Williams-Watts Model (KWW) algorithm for photon diffusion to the physiologic signal.

11. The method of claim 10, comprising determining an absorption rate of a sample of the patient from the physiologic signal.

12. The method of claim 11, comprising applying a predicted KWW model of diffuse reflectance when the absorption rate is determined to fall below a threshold value.

13. The method of claim 12, comprising calculating the threshold value based at least in part upon the physiologic signal.

14. The method of claim 11, comprising applying a predicted Beer-Lambert model of diffuse reflectance when the absorption rate is determined to be above a threshold value.

15. The method of claim 14, comprising storing the threshold value as a preprogrammed value.

16. The method of claim 10, wherein calculating physiological characteristics of a sample comprises utilizing the mixed Beer-Lambert/KWW algorithm to determine concentrations of chromophores in a sample area of the patient.

17. The method of claim 10, wherein obtaining a physiologic signal comprises: emitting electromagnetic radiation into a tissue sample of the patient; detecting the scattered and/or reflected light from the tissue sample; generating the physiologic signal corresponding to the scattered and/or reflected light detected and
directing the physiologic signal to the monitor.

* * * * *